(12) United States Patent
Levine

(10) Patent No.: US 6,430,441 B1
(45) Date of Patent: Aug. 6, 2002

(54) IMPLANTABLE CARDIAC STIMULATION DEVICE HAVING AUTOCAPTURE/ AUTOTHRESHOLD CAPABILITY

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/483,908

(22) Filed: Jan. 18, 2000

(51) Int. Cl.⁷ ............................................... A61N 1/362
(52) U.S. Cl. ......................................................... 607/28
(58) Field of Search ................................. 607/28, 9, 11, 607/14, 27

(56) References Cited

U.S. PATENT DOCUMENTS

| | | | |
|---|---|---|---|
| 4,712,555 A | 12/1987 | Thornander et al. | 128/419 |
| 4,788,980 A | 12/1988 | Mann et al. | 128/419 |
| 4,809,697 A | 3/1989 | Causey, III et al. | 128/419 |
| 4,940,052 A | 7/1990 | Mann et al. | 128/419 |
| 4,944,298 A | 7/1990 | Sholder | 128/419 |
| 4,944,299 A | 7/1990 | Silvian | 128/419 |
| 5,391,192 A | 2/1995 | Lu et al. | 607/28 |
| 5,458,623 A * | 10/1995 | Lu et al. | |
| 5,476,486 A | 12/1995 | Lu et al. | 607/28 |
| 5,861,012 A * | 1/1999 | Stroebel | |
| 6,175,766 B1 * | 1/2001 | Bornzin | |
| 6,263,244 B1 * | 7/2001 | Mann | |

* cited by examiner

Primary Examiner—Kennedy Schaetzle

(57) ABSTRACT

An improved system and method for performing autocapture/autothreshold detection in an implantable cardiac stimulation device or any device capable of stimulating some organ or tissue in the body. In some existing systems, loss-of-capture and capture decisions are based upon two consecutive cardiac events. However, such systems may be subject to subthreshold stimulation pulses that capture and lose capture on alternating pulses, trigeminy PVC sequences, or the like that require a higher stimulation pulse amplitude but cannot make this determination due to the two consecutive event requirement. Accordingly, in the present invention, the determination of whether there is a loss-of-capture is determined only according to paced events, i.e., ignoring intrinsic and PVC beats. Furthermore, the loss-of-capture determination is based upon X out of the last Y beats, where Y is greater than 2 and X is less than Y. Accordingly, consecutive loss-of-capture events are no longer required in determining the threshold level. In a further aspect, a preferred embodiment monitors cardiac events to detect a sequence of patterns that could indicate a trigeminy pattern and, if detected, the pacing rate is increased to attempt to break the pattern and thus permit the threshold level to be detected.

41 Claims, 9 Drawing Sheets

IMPLANTABLE CARDIAC STIMULATION DEVICE HAVING AUTOCAPTURE/ AUTOTHRESHOLD CAPABILITY

FIELD OF THE INVENTION

The present invention is generally directed to an implantable medical device, e.g., a cardiac stimulation device, and is particularly directed to an autocapture/autothreshold pacing system and method for use in such a device.

BACKGROUND OF THE INVENTION

Implantable cardiac stimulation devices are well known in the art. They include implantable pacemakers which provide stimulation pulses to cause a heart, which would normally beat too slowly or at an irregular rate, to beat at a controlled normal rate. They also include defibrillators which detect when the atria and/or the ventricles of the heart are in fibrillation or a pathologic rapid organized rhythm and apply cardioverting or defibrillating electrical energy to the heart to restore the heart to a normal rhythm. Implantable cardiac stimulation devices may also include the combined functions of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation pulses when they are needed and inhibit the delivery of cardiac stimulation pulses at other times. This inhibition accomplishes two primary functions. Firstly, when the heart is intrinsically stimulated, its hemodynamics are generally improved. Secondly, inhibiting the delivery of a cardiac stimulation pulse reduces the battery current drain on that cycle and extends the life of the battery which powers and is located within the implantable cardiac stimulation device. Extending the battery life, will therefore delay the need to explant and replace the cardiac stimulation device due to an expended battery. Generally, the circuitry used in implantable cardiac stimulation devices have been significantly improved since their introduction such that the major limitation of the battery life is primarily the number and amplitude of the pulses being delivered to a patient's heart. Accordingly, it is preferable to minimize the number of pulses delivered by using this inhibition function and to minimize the amplitude of the pulses where this is clinically appropriate.

It is well known that the amplitude value of a pulse that will reliably stimulate a patient's heart, i.e., its threshold value, will change over time after implantation and will vary with the patient's activity level and other physiological factors. To accommodate for these changes, pacemakers may be programmed to deliver a pulse at an amplitude well above (by an increment or a factor) an observed threshold value. To avoid wasting battery energy, the capability was developed to automatically adjust the pulse amplitude to accommodate for these long and short term physiological changes. In an existing device, the Affinity™ DR, Model 5330 L/R Dual-Chamber Pulse Generator, manufactured by the assignee of the present invention, an AutoCapture™ pacing system is provided. The User's Manual, ©1998 St. Jude Medical, which describes this capability is incorporated herein by reference. In this system, the threshold level is automatically determined in a threshold search routine and is maintained by a capture verification routine. Once the threshold search routine has determined a pulse amplitude that will reliably stimulate, i.e., capture, the patient's heart, the capture verification routine monitors signals from the patient's heart to identify pulses that do not stimulate the patient's heart (indicating a loss-of-capture). Should a loss-of-capture (LOC) occur, the capture verification routine will generate a large amplitude (e.g., 4.5 volt) backup pulse shortly after (typically within 80–100 ms) the original (primary) stimulation pulse. This capture verification occurs on a pulse-by-pulse basis and thus, the patient's heart will not miss a beat. However, while capture verification ensures the patient's safety, the delivery of two stimulation pulses (with the second stimulation pulse typically being much larger in amplitude) is potentially wasteful of a limited resource, the battery capacity. To avoid this condition, the existing device, monitors for two consecutive loss-of-capture events and only increases the amplitude of the primary stimulation pulse should two consecutive loss-of-capture (LOC) events occur. This procedure is repeated, if necessary, until two consecutive pulses are captured, at which time a threshold search routine will occur. The threshold search routine decreases the primary pulse amplitude until capture is lost on two consecutive pulses and then, in a similar manner to that previously described, increases the pulse amplitude until two consecutive captures are detected. This is defined as the capture threshold. The primary pulse amplitude is then increased by a working margin value to ensure a primary pulse whose amplitude will exceed the threshold value and thus reliably capture the patient's heart without the need for frequent backup pulses.

While the method used by this existing device has been proven to be a safe and effective method of determining a primary pulse amplitude that will reliably capture the patient's heart, conditions have been encountered that may cause the prior art system to rely upon backup pulses for extended periods of time, thus expending battery capacity to ensure patient safety. For example, in one case, a pulse amplitude may be set just below the threshold of a patient's heart (see the first portion of FIG. 8). Due to various factors, e.g., electrical noise, myopotentials or the like, the prior art system may alternate between capture and loss-of-capture events for an extended period of time. In a next case (see FIG. 9), a heart may be subject to periods of PVCs (premature ventricular contractions) generated by ectopic foci in the heart. Following a PVC, the heart muscle may be subject to supernormal conduction due to a longer repolarization period. Accordingly, an otherwise subthreshold primary pulse may still be capable of causing capture of the patient's heart for the next cardiac cycle. Accordingly, a trigeminy type pattern that alternates between loss-of-capture, a PVC (appearing as a sensed event), and a captured pulse may repeatedly occur. Since such a pattern does not satisfy the two sequential loss-of-capture event requirement of the existing device, the existing device will not be able to adapt to this condition. Although, patient safety is maintained, it is done at the expense of battery life.

Therefore what is needed is a flexible system that can determine a threshold amplitude for the primary pulse in such special cases as well as normal cases and that can preferably minimize the time to determine the threshold amplitude.

SUMMARY OF THE INVENTION

The present invention provides an improved system and method for performing autocapture and autothreshold detection in an implantable cardiac stimulation device. In some prior art systems, loss-of-capture and capture decisions are based upon single events. Such a single event system would generally be overly sensitive and would tend to determine unnecessarily high threshold values. In other systems, lossof-capture and capture decisions are based upon two consecutive events. These systems additionally include a large amplitude backup pulse capability to stimulate the patient's heart when there is a loss-of-capture and there would otherwise be a missed heart beat. However, such systems may be subject to subthreshold stimulation pulses that capture and lose capture on alternating pulses, trigeminy PVC sequences, or the like that require a higher stimulation pulse amplitude but cannot make this determination due to the failure to meet the two consecutive event requirement.

Accordingly, in a first aspect of the present invention, the determination of whether there is a loss-of-capture is determined only according to paced cardiac cycles, i.e., ignoring intrinsic and PVC beats. In a second aspect of the present invention, the determination of whether there is a loss-of-capture is based upon X out of the last Y heart beats (i.e., cardiac events), where Y is a value greater than 2 and X is a value less than Y. In a typical example, a loss-of-capture determination is whether there was a loss-of-capture for 2 (X) out of the last 3 (Y) paced beats. Accordingly, consecutive loss-of-capture events are no longer required in determining the threshold level.

In a further aspect of the present invention, a preferred embodiment monitors cardiac events to detect a sequence of patterns that could indicate a trigeminy or bigeminy pattern and, if detected, the pacing rate is increased to attempt to break the pattern and thus permit the threshold level to be detected.

A preferred embodiment of an implantable cardiac stimulation device for stimulating a patient's heart during each cardiac cycle through at least one electrode implanted in electrical contact with selected cardiac tissue comprises: (1) a pulse generator electrically coupled to the electrode and configured to generate stimulation pulses at a controlled amplitude and rate to thereby stimulate the patient's heart; (2) a detection circuit electrically coupled to the electrode and configured to receive cardiac signals for determining the presence or absence of an evoked response to each of the stimulation pulses; and (3) a controller coupled to the pulse generator for increasing the stimulation pulse amplitude when a first specified criteria has been met, wherein the first specified criteria is the absence of evoked responses from X out of the last Y stimulation pulses where Y is a value greater than 2 and X is a value less than Y.

In a further aspect of the present invention means are provided to detect a sequence of responses from a sample window which corresponds to whether there were captured cardiac events during each of the cardiac cycles in the sample window. When N contiguous occurrences of a specified M response sequence are detected in the sample window, the controller is configured to increase the controlled stimulation rate.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention is directed to an improved system and method for performing autocapture and autothreshold detection in an implantable cardiac stimulation device, e.g., a pacemaker or an ICD. In some prior art systems, loss-of-capture and capture decisions are based upon single events. Such a single event system would generally be overly sensitive and would tend to determine unnecessarily high threshold values. In other systems, loss-of-capture and capture decisions are based upon two consecutive cardiac events. These systems additionally include a large amplitude backup pulse capability to stimulate the patient's heart when there is a loss-of-capture and there would otherwise be a missed heart beat. However, such systems may be subject to subthreshold stimulation pulses that capture and lose capture on alternating pulses, trigeminy PVC sequences, or the like that require a higher stimulation pulse amplitude but cannot make this determination due to the two consecutive event requirement.

Accordingly, in a first aspect of the present invention, the determination of whether there is a loss-of-capture is determined only according to paced cardiac events, i.e., ignoring intrinsic and PVC beats which occurred during a cardiac cycle. In a second aspect of the present invention, the determination of whether there is a loss-of-capture is based upon X out of the last Y heart beats (i.e., cardiac events), where Y is a value greater than 2 and X is a value less than Y. In a typical example, a loss-of-capture determination is whether there was a loss-of-capture for 2 (X) out of the last 3 (Y) paced beats. Accordingly, consecutive loss-of-capture events are no longer required in determining the threshold level.

In a further aspect of the present invention, a preferred embodiment monitors cardiac events to detect a sequence of patterns that could indicate a trigeminy pattern and, if detected, the pacing rate is increased to attempt to break the pattern and thus permit the threshold level to be detected.

As indicated above, the present invention may be used with various types of implantable stimulation devices for stimulating cardiac tissue, including an implantable pacemaker configured to treat bradycardia and/or tachycardia, an implantable cardioverter-defibrillator (ICD), or a combination thereof or any other device capable of stimulating other body tissues and recognizing the response to the delivered stimulus. Such devices control/monitor the operations of a patient's heart or other body tissues.

Figure 1:
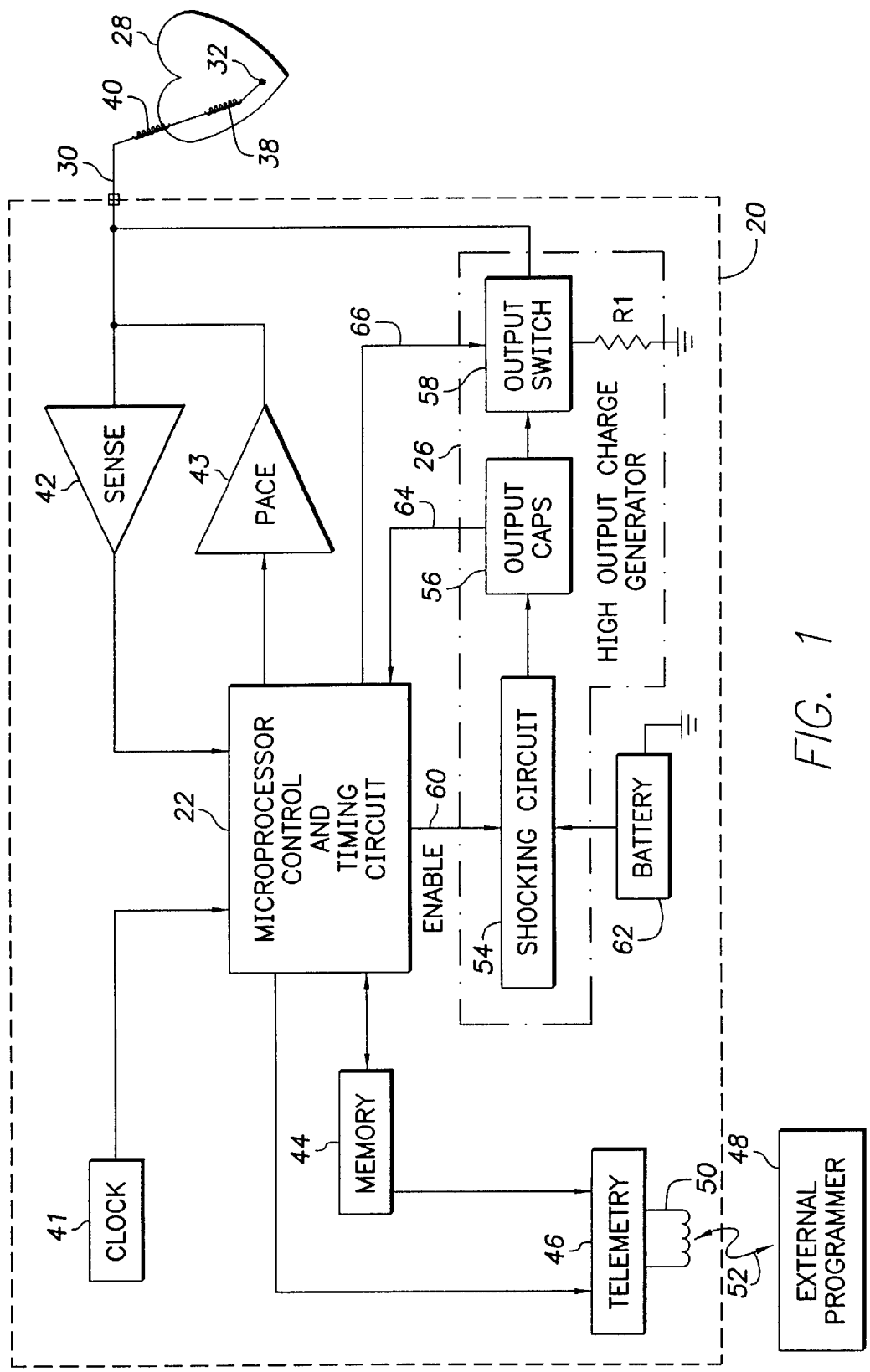
FIG. 1 shows a simplified functional block diagram of an implantable cardioverter/defibrillator (ICD), which represents one type of implantable cardiac stimulation device with which the present invention may be used.
Figure 2:
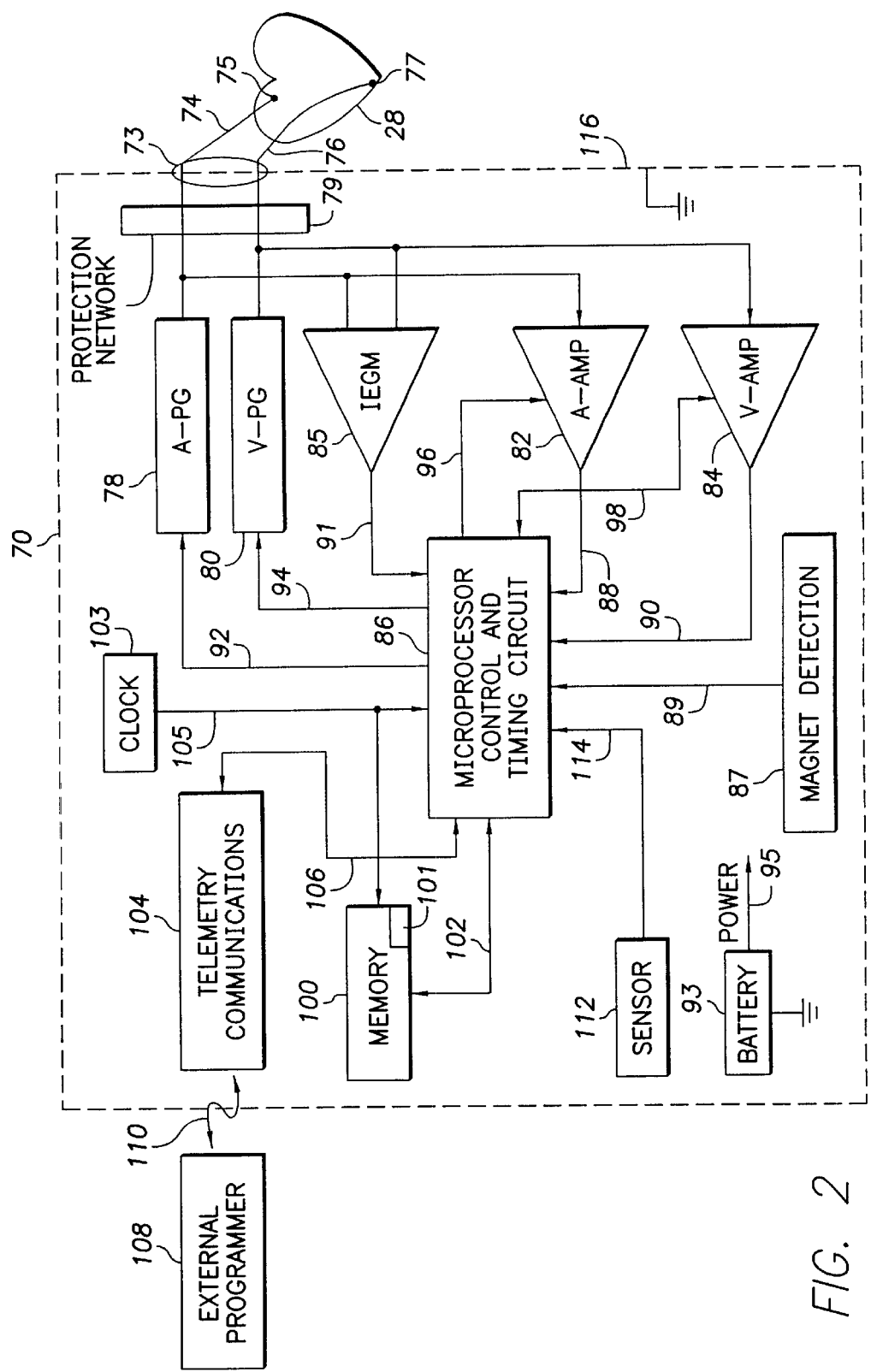
FIG. 2 shows a functional block diagram of an implantable dual-chamber pacemaker, which represents another type of implantable medical device with which the invention may be used.

To better understand the invention, it will first be helpful to have an understanding of the basic functions performed by exemplary implantable stimulation devices with which the invention may be used, e.g., an ICD with dual chamber coils (see FIG. 1) and/or a dual-chamber pacemaker (see FIG. 2). While a dual-chamber device has been chosen for this description, this is for teaching purposes only. It is recognized that the present invention could be implemented into a single-chamber device, that one of skill in the art could readily adapt the dual-chamber device shown in FIG. 2 to perform single-chamber functionality, and that a single-chamber device is within the spirit of the invention as is any device capable of delivering stimulating impulses to a tissue or organ of the body.

In FIG. 1, there is shown a simplified functional block diagram of an ICD device 20, and in FIG. 2, there is shown a simplified functional block diagram of a dual-chamber pacemaker 70. It should also be noted that, in some instances, the functions of an ICD and a pacemaker may be combined within the same cardiac stimulation device. However, for teaching purposes, the devices will be described separately.

It is the primary function of an ICD device to sense the occurrence of a tachyarrhythmia and to automatically apply an appropriate electrical shock therapy to the heart aimed at terminating the tachyarrhythmia. To this end, the ICD device 20, as shown in the functional block diagram of FIG. 1, includes a control and timing circuit (hereinafter referred to as a control/timing circuit) 22, such as a microprocessor, state-machine or other such control circuitry, that controls a high output charge generator 26. The high output charge generator 26 generates electrical stimulation pulses of moderate or high energy (corresponding to cardioversion or defibrillation pulses, respectively), e.g., electrical pulses having energies of from 1 to 10 joules (moderate) or 11 to 40 joules (high), as controlled by the control/timing circuit 22.

Such moderate or high energy pulses are applied to the patient's heart 28 through at least one lead 30 having at least two defibrillation electrodes, such as coil electrodes 38 in the atrium and 40 in the superior vena cava. The lead 30 preferably also includes at least one electrode for pacing and sensing functions, such as electrode 32. Typically, the lead 30 is transvenously inserted into the heart 28 so as to place the coil electrodes 38 and 40 where they are in electrical and preferably physical contact with the patient's heart 28. While only one lead is shown in FIG. 1, it is to be understood that additional defibrillation leads and electrodes may be used to apply the shock treatment generated by the high voltage generator 26 to the patient's heart 28.

The ICD 20 also includes a sense amplifier 42 that is coupled to at least one sensing electrode 32. It is the function of the sense amplifier 42 to sense the electrical activity of the heart 28, as is known in the art, such as R-waves which are the surface ECG representation of ventricular depolarizations which result in the contraction of ventricular tissue, and P-waves which are the surface ECG manifestations of atrial depolarizations which result in the contraction of atrial tissue. Thus, by sensing the ventricular and/or atrial depolarizations (manifested by the R-waves and/or P-waves on the surface ECG) through the sense amplifier 42, the control/timing circuit 22 is able to make a determination as to the rate and regularity of the patient's heart beat. Such information, in turn, allows the control/timing circuit 22 to determine whether the patient's heart 28 is experiencing an arrhythmia, and to apply appropriate stimulation therapy. Alternatively, a pacing pulse generator 43 can be used to pace the heart in accordance with a preselected pacing strategy. To accomplish this task, the amplitude of pacing pulses generated by the pulse generator 43 is set by the physician to a value above the threshold level for the patient's heart to ensure capture, i.e., successful stimulation of the patient's heart.

The control/timing circuit 22 further has a memory circuit 44 coupled thereto wherein the operating parameters used by the control/timing circuit 22 are stored. Such operating parameters define, for example, the amplitude of each shocking pulse to be delivered to the patient's heart 28 as well as the duration of these shock pulses. The memory 44 may take many forms, and may be subdivided into as many different memory blocks or sections (addresses) as needed to store desired data and control information. A feature of an exemplary ICD 20 is the ability to sense and store a relatively large amount of data as a data record, which data record may then be used to guide the operation of the device, i.e., the present operating mode of the device may be dependent, at least in part, on past performance data.

Advantageously, the operating parameters of the implantable device 20 may be non-invasively programmed into the memory 44 through a telemetry circuit 46, in telecommunicative contact with an external programmer 48 by way of a suitable coupling coil 50. The coupling coil 50 may serve as an antenna for establishing a radio frequency (RF) communication link 52 with the external programmer 48, or the coil 50 may serve as a means for inductively coupling data between the telemetry circuit 46 and the external programmer 48, as is known in the art. See, e.g., U.S. Pat. No. 4,809,697 (Causey, III et al.) and U.S. Pat. No. 4,944, 299 (Silvian), incorporated herein by reference. Further, such telemetry circuit 46 advantageously allows status information relating to the operation of the ICD 20, as contained in the control/timing circuit 22 or memory 44, to be sent to the external programmer 48 through the established link 52.

The control/timing circuit 22 includes appropriate processing and logic circuits for analyzing the output of the sense amplifier 42 and determining if such signals indicate the presence of an arrhythmia. Typically, the control/timing circuit 22 is based on a microprocessor, or similar processing circuit, which includes the ability to process or monitor input signals (data) in a prescribed manner, e.g., as controlled by program code stored in a designated area or block of the memory 44. The details of the design and operation of the control/timing circuit 22 are not critical to the present invention. Rather, any suitable control/timing circuit 22 may be used that performs the functions described herein. The use, design, and operation of microprocessor-based control circuits to perform timing and data analysis functions is known in the art.

The ICD 20 additionally includes a battery 62 which provides operating power to all of the circuits of the ICD 20.

In FIG. 2, a simplified block diagram of the circuitry needed for a dual-chamber pacemaker 70 is illustrated. The pacemaker 70 is coupled to heart 28 by way of leads 74 and 76, the lead 74 having an electrode 75 that is in electrical and preferably physical contact with one of the atria of the heart 28, and the lead 76 having an electrode 77 that is in electrical and preferably physical contact with one of the ventricles of the heart 28. The leads 74 and 76 are electrically and physically connected to the pacemaker 70 through a connector 73 that forms an integral part of the housing wherein the circuits of the pacemaker are housed. Typically, leads 74 and 76 are operated in a bipolar mode where a "tip" portion provides the voltage signal that provides current that flows to a "ring" portion on the same lead. Alternatively, leads 74 and 76 can operate in a unipolar mode where current flows from the "tip" portion of each lead to a conductive case 116 which surrounds the pacemaker device 70.

The connector 73 is electrically connected to a protection network 79, which network 79 electrically protects the circuits within the pacemaker 70 from excessive shocks or voltages that could appear on the electrodes 75 and/or 77 in the event such electrodes were to come in contact with a high voltage signal, e.g., from a defibrillation shock.

The leads 74 and 76 carry stimulation pulses to the electrodes 75 and 77 from an atrial pulse generator (A-PG) 78 and a ventricular pulse generator (V-PG) 80, respectively. Further, electrical signals from the atria are carried from the electrode 75, through the lead 74, to the input terminal of an atrial channel sense amplifier (A-AMP) 82; and electrical signals from the ventricles are carried from the electrode 77, through the lead 76, to the input terminal of a ventricular channel sense amplifier (V-AMP) 84. Similarly, electrical signals from both the atria and ventricles are applied to the inputs of an intracardiac electrogram amplifier (IEGM) 85. The amplifier 85 is typically configured to detect an evoked response from the heart 28, i.e., a response to an applied stimulation pulse, thereby aiding in the detection of "capture". Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue. Following each captured stimulation pulse, the associated cardiac tissue (i.e., the atria or the ventricles) enters into a physiologic refractory period during which it cannot be re-stimulated.

The dual-chamber pacemaker 70 is controlled by a control and timing circuit (hereinafter referred to as a control/timing circuit) 86 that typically includes a microprocessor programmed to carry out control and timing functions. The control/timing circuit 86 receives the sensed signals from the atrial (A-AMP) amplifier 82 over signal line 88. Similarly, the control/timing circuit 86 receives the output signals from the ventricular (V-AMP) amplifier 84 over signal line 90, and the output signals from the IEGM amplifier 85 over signal line 91. These output signals which indicate capture due to an evoked response are generated each time that a P-wave or an R-wave is sensed within the heart 28. The control/timing circuit 86 also generates trigger signals that are sent to the atrial pulse generator (A-PG) 78 and the ventricular pulse generator (V-PG) 80 over signal lines 92 and 94, respectively, to control the amplitude and duration of the signals delivered to the electrodes, 75 and 77. These trigger signals are generated each time that a stimulation pulse is to be generated by the respective pulse generator 78 or 80. The atrial trigger signal is referred to simply as the "A-trigger", and the ventricular trigger signal is referred to as the "V-trigger".

During the time that either an A-pulse or V-pulse is being delivered to the heart, the corresponding sense amplifier, A-AMP 82 and/or V-AMP 84, is typically disabled by way of a blanking signal presented to these amplifiers from the control/timing circuit 86 over signal lines 96 and 98, respectively. This blanking action prevents the amplifiers 82 and 84 from becoming saturated from the relatively large stimulation pulses that are present at their input terminals during this time. This blanking action also helps prevent residual electrical signals present in the muscle tissue as a result of the pacemaker stimulation from being interpreted as P-waves or R-waves.

As shown in FIG. 2, the pacemaker 70 further includes a memory circuit 100 that is coupled to the control/timing circuit 86 over a suitable data/address bus 102. This memory circuit 100 allows certain control parameters, used by the control/timing circuit 86 in adjusting or programming the operation of the pacemaker 70, to be stored and modified, as required, in order to customize the pacemaker's operation to suit the needs of a particular patient. Further, data regarding the operation of the pacemaker 70 (sensed or paced events and activation of any special algorithms or results of interventions) may be stored in the memory 100 for later retrieval and analysis.

As with the memory 44 of the ICD device 20 shown in FIG. 1, the memory 100 of the pacemaker 70 (FIG. 2) may take many forms and may be subdivided into as many different memory blocks or sections (addresses) as needed in order to allow desired data and control information to be stored. A feature of an exemplary cardiac stimulation device is the ability to store a relatively large amount of sensed data as a data record, which data record may then be used to guide the operation of the device. That is, the operating mode of the pacemaker may be dependent, at least in part, on past performance data. For example, an average atrial rate may be determined based on the sensed atrial rate over a prescribed period of time. This average rate may then be stored and updated at regular intervals. Such stored rate may then be compared to a present atrial rate and, depending upon the difference, used to control the operating mode of the pacemaker. Other parameters, of course, in addition to (or in lieu of) atrial rate, may be similarly sensed, stored, averaged (or otherwise processed), and then used for comparison purposes against one or more currently-sensed parameters. Advantageously, modern memory devices allow for the storage of large amounts of data in this manner.

A clock circuit 103 directs an appropriate clock signal(s) to the control/timing circuit 86, as well as to any other needed circuits throughout the pacemaker 70 (e.g., to the memory 100) by way of clock bus 105.

A telemetry/communications circuit 104 is further included in the pacemaker 70. This telemetry circuit 104 is connected to the control/timing circuit 86 by way of a suitable command/data bus 106. In turn, the telemetry circuit 104, which is included within the implantable pacemaker 70, may be selectively coupled to an external programmer 108 by means of an appropriate communication link 110. The communication link 110 may be any suitable electromagnetic link such as an RF (radio frequency) channel, a magnetic link, an inductive link, an optical link, and the like. Advantageously, desired commands may be sent to the control/timing circuit 86 through the external programmer 108 and the communication link 110. Similarly, through this communication link 110 with the programmer 108, data commands (either held within the control/timing circuit 86, as in a data latch, or stored within the memory 100) may be remotely received from the programmer 108. Similarly, data initially sensed through the leads 74 or 76, and processed by the microprocessor control circuits 86, or other data measured within or by the pacemaker 70, may be stored and uploaded to the programmer 108. In this manner, non-invasive communications can be established with the implanted pacemaker 70 from a remote, non-implanted, location.

The pacemaker 70 additionally includes a battery 93 which provides operating power to all of the circuits of the pacemaker 70 via a power signal line 95.

It is noted that the pacemaker 70 in FIG. 2 is referred to as a dual-chamber pacemaker because it interfaces with both the atria and the ventricles of the heart 28. Those portions of the pacemaker 70 that interface with the atria, e.g., the lead 74, the P-wave sense amplifier 82, the atrial pulse generator 78, and corresponding portions of the control/timing circuit 86, are commonly referred to as the "atrial channel". Similarly, those portions of the pacemaker 70 that interface with the ventricles, e.g., the lead 76, the R-wave sense amplifier 84, the ventricular pulse generator 80, and corresponding portions of the control/timing circuit 86, are commonly referred to as the "ventricular channel". While a dual chamber pacemaker includes a single atrial channel and a single ventricular channel, multichamber devices may include more than one atrial channel and/or more than one ventricular channel.

As needed for certain applications, the pacemaker 70 may further include at least one sensor 112 that is connected to the control/timing circuit 86 of the pacemaker 70 over a suitable connection line 114. While this sensor 112 is illustrated in FIG. 2 as being included within the pacemaker 70, it is to be understood that the sensor may also be external to the pacemaker 70, yet still be implanted within or carried by the patient. A common type of sensor is an activity sensor, such as a piezoelectric crystal, that is mounted to the case of the pacemaker. Other types of sensors are also known, such as sensors that sense the oxygen content of blood, respiration rate, pH of blood, body motion, and the like. The type of sensor used is not critical to the present invention. Any sensor or combination of sensors capable of sensing a physiological or physical parameter relatable to the rate at which the heart should be beating (i.e., relatable to the metabolic need of the patient), and/or relatable to whether a tachyarrhythmia is likely to soon occur, can be used. Such sensors are commonly used with "rate-responsive" or "rate-modulated" pacemakers in order to adjust the rate (pacing cycle) of the pacemaker in a manner that tracks the physiological or metabolic needs of the patient.

The pacemaker 70 further includes magnet detection circuitry 87, coupled to the control/timing circuit 86 over signal line 89. It is the purpose of the magnet detection circuitry 87 to detect when a magnet is placed over the pacemaker 70. The magnet may be used by a physician or other medical personnel to perform various reset functions of the pacemaker 70 and/or to signal the control/timing circuit 86 that an external programmer 108 is in place to receive data from, or send data to, the pacemaker memory 100 or control/timing circuit 86 through the telemetry communications circuit 104.

As with the ICD device 20 of FIG. 1, the telemetry or communications circuit 104 may be of conventional design, such as is described in U.S. Pat. No. 4,944,299, or as is otherwise known in the art. Similarly, the external programmer 108 may be of any suitable design known in the art, such as is described in U.S. Pat. No. 4,809,697. Likewise, the memory circuit 100, and the circuits utilized in the atrial and ventricular channels may all be of common design as is known in the pacing art. The present invention is not concerned with the details of the circuitry utilized for each of these pacing elements. Rather, it is concerned with the manner in which the amplitude of the pacing pulses delivered to the heart is determined in coordination with autocapture and autothreshold modes of operation. Such determination is controlled by the control/timing circuit 86.

The control/timing circuit 86 may be realized using a variety of different techniques and/or circuits. The preferred type of control/timing circuit 86 is a microprocessor-based control/timing circuit. It is noted, however, that the control/timing circuit 86 could also be realized using a state machine. Indeed, any type of control/timing circuit or system could be employed for the control/timing circuit 86. The present invention is likewise not concerned with the details of the control/timing circuits 22 and 86. Rather, it is concerned with the end result achieved by the control/timing circuit. That is, so long as the control/timing circuit 86 controls the operation of the pacemaker (or other medical device) so that the desired functions are achieved as set forth herein, it matters little what type of control/timing circuit is used. Those of skill in the implantable medical device art, given the teachings presented herein, should thus be able to fashion numerous different types of control/timing circuits that achieve the desired device control.

Representative of the types of control/timing circuits that may be used with the invention is the microprocessor-based control/timing circuit described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are incorporated herein by reference.

Figure 3:
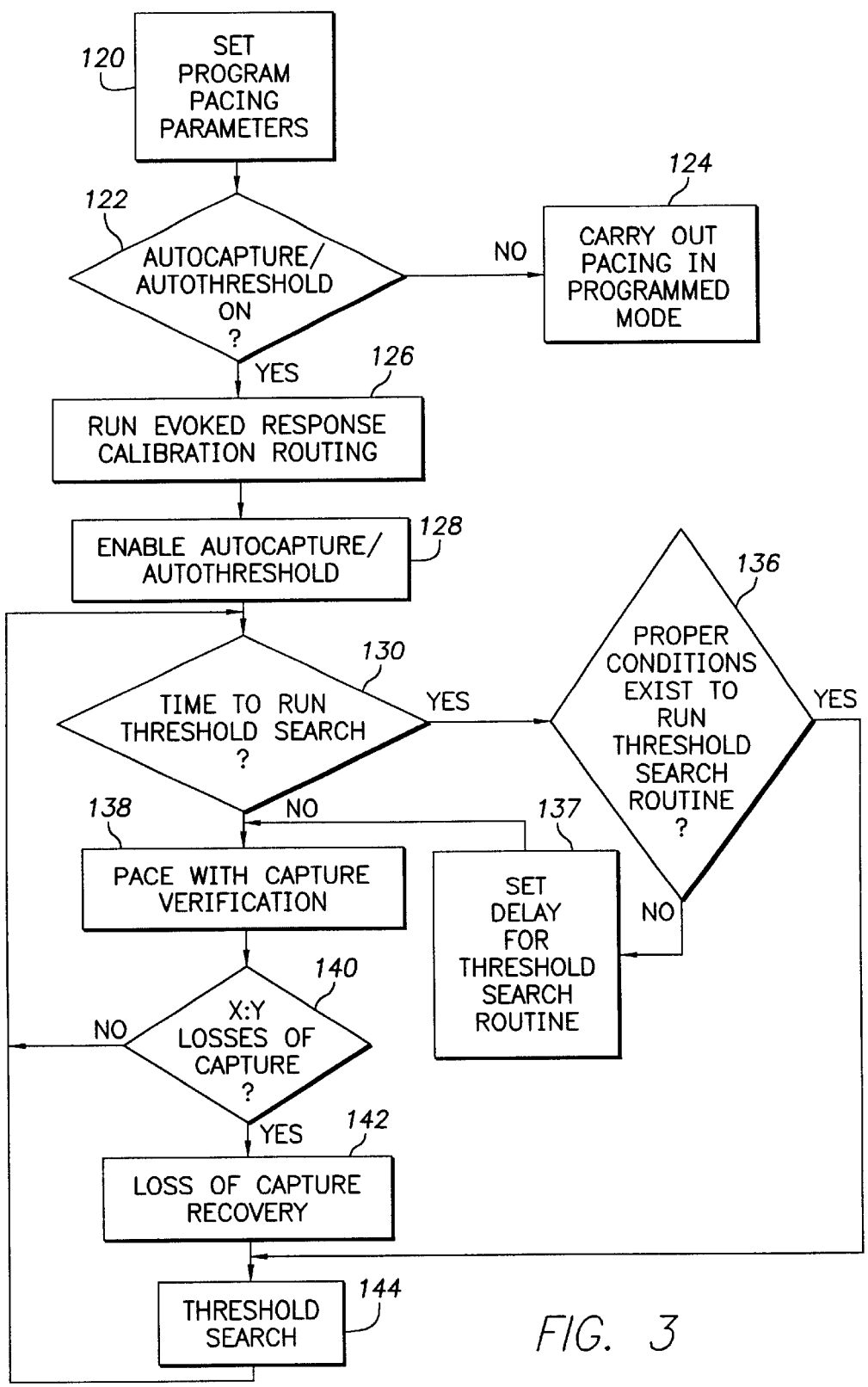
FIG. 3 is a simplified top level flow diagram of the autocapture/autothreshold method of the present invention using an improved criteria for determining loss-of-capture and capture.

FIG. 3 is a simplified top level flow diagram of the autocapture/autothreshold method of the present invention using an improved criteria for determining loss-of-capture and capture. To simplify the discussion, this method is described in reference to the dual-chamber pacemaker 70 of FIG. 2. In this case, the autocapture/autothreshold routines preferably monitor and adjust the amplitude of a ventricular pacing pulse in response to whether an evoked response is sensed. However, one of ordinary skill in the art would recognize the applicability of this method to other such implantable cardiac stimulation devices, e.g., the atrial channel of a dual chamber pacemaker or the ICD 20 of FIG. 1. Initially in block 120, all of the pacing parameters required by the pacemaker to operate in a desired program mode are set from values in memory 100 or by way of the external programmer 108. In addition to conventional pacing parameters, parameters related to practicing the present invention are preferably preprogrammed and include a definition of: the size of the increase or decrease of the primary pulse, i.e., the ventricular pacing pulse delivered from the ventricular pulse generator 80, used by the autocapture/autothreshold routines; how often the periodic autothreshold search routine is to be invoked (e.g., once a day, every 90 minutes, etc.); and a functional or working factor. The working factor is used during the loss-of-capture recovery routine as well as during the autothreshold search routine and defines how much above the determined capture threshold the ventricular pulse amplitude is to be set to provide maintenance of capture during the normal course of events. In a preferred device, these parameters include decreased AV (e.g., 50 ms) and PV (e.g., 25 ms) delays to be used during the autothreshold routine to cause the ventricular stimulation pulse to be issued prior to a potential intrinsic R-wave. This decreased delay allows the heart to respond to stimulation pulses since the stimulation pulses will precede any intrinsic beats after which ventricular tissue would be refractory and additionally, it helps to avoid fusion beats. While these preprogrammed parameters are relevant to the present invention, they are also relevant to the general operation of the pacemaker 70 and thus are set using routine methods, well known to those of skill in the art. Additionally, the loss-of-capture and capture criteria used by the present invention are set within block 120. These criteria will be discussed in greater detail below.

Assuming that all of the pacing parameters were set in block 120, a first determination is made in block 122 as to whether autocapture/autothreshold is enabled. If the autocapture/autothreshold routine has not been enabled (the NO branch of block 122), the pacemaker 70 resumes cardiac pacing in the desired programmed mode in block 124.

If autocapture/autothreshold has been enabled (the YES branch of block 122), the sensitivity of the atrial 82 and ventricular 84 amplifiers are adjusted in an evoked response calibration routine in block 126. As is known in the art, the evoked response calibration routine adjusts the evoked response detection sensitivity after measuring the polarization caused by a pacing pulse delivered during the natural refractory period of the heart and the evoked response signal amplitude.

After the autocapture/autothreshold routine has been enabled in block 128, a determination is made in block 130 as to whether it is time to initiate a periodic running of the threshold search routine. Typically, the threshold search routine 144 will start automatically at a specified frequency which can be preset in the device or a programmable parameter, e.g., once a day, every 90 minutes, etc. Also, the threshold search routine 144 may be triggered by the completion of the loss-of-capture recovery routine 142 (described below).

If it is time to start the threshold search routine 144 (the YES branch of block 130), then a first step is to verify in block 136 that proper conditions exist to accurately perform the threshold search routine (the YES branch of block 136). In general, such conditions require that the pacemaker 70 be engaged in ventricular pacing (generating V-pulses from the ventricular pulse generator 80) at a rate that is below the maximum tracking rate. If the ventricular pulse generator is at the maximum tracking rate, then the proper conditions for executing the threshold search routine 144 do not exist (the NO branch of block 136). As such, the threshold search routine 144 is delayed for a prescribed amount of time in block 137, during which delay the pacemaker 70 continues to operate in its present programmed mode and at its present output level. Otherwise, the threshold search routine 144 begins. Details of the threshold search routine 144 are provided below.

If it is not time to commence the threshold search routine 144 (the NO branch of block 130), the pacemaker 70 proceeds to execute the capture verification routine 138 in conjunction with the present pacing mode.

When initiated, the capture verification routine 138 (see FIG. 4) is a continuously running program that performs a loss-of-capture criteria test for each stimulation pulse generated during the programmed pacing sequence. Essentially, as discussed further below, the capture verification routine 138 determines for each cardiac cycle whether there was an evoked response corresponding to each stimulation pulse. If an evoked response is sensed at block 162, a capture count (C) is incremented at block 164 to track the number of captured pulses. If an evoked response is not sensed after a prescribed period of time (e.g., 60 ms) subsequent to the stimulation pulse, a backup pulse is issued in block 166 and the backup count (B) is incremented in block 168 to track the number of non-captured pulses that required a backup pulse to ensure a heart beat during a cardiac cycle. Alternatively, a cardiac event may be sensed before the stimulation pulse is issued, i.e., during the PV delay, that could correspond to an intrinsic R-wave or a premature ventricular contraction (PVC). Such a cardiac event causes the intrinsic count (I) to be incremented in block 154 to track the number of such intrinsic events, events that did not require a stimulation pulse. By processing these counts (as described further below), a determination is made in block 140 as to whether X out of the last Y stimulation pulses (described as X:Y) resulted in a loss-of-capture. In the prior art, this required two consecutive loss-of-capture events, i.e., 2:2, or two consecutive backup pulses (designated, herein as a BB sequence). However, in the present invention, this criteria is expanded to include X loss-of-capture events out of the last Y stimulation pulses, where Y is greater than 2 and X is less than Y.

The significance of this improved criteria is shown in the following examples. In embodiments of this invention, each cardiac cycle results in either a captured stimulation pulse, designated as a C event and counted in block 164, a loss-of capture with a precautionary backup pulse, designated as a B event and counted in block 168, or an intrinsic event, e.g., an intrinsic beat or a PVC occurring without a stimulation pulse, designated as an I event and counted in block 154. Sequences of these cardiac events, events occurring in sequential cardiac cycles are described herein as sequences of C, B and I events or cardiac responses.

Figure 8:
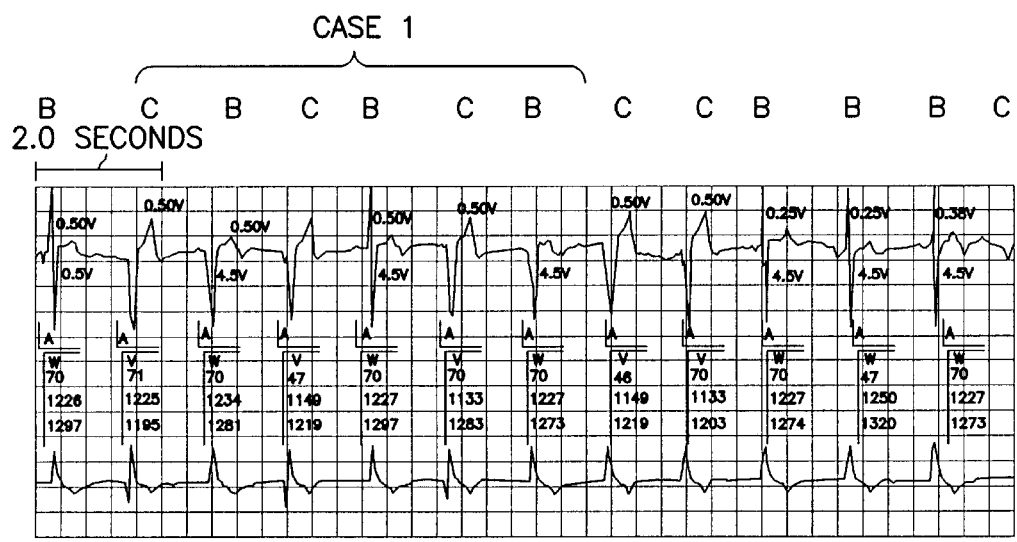
FIG. 8 is an exemplary intracardiac electrogram showing an alternating sequence of capture and loss-of-capture events, a sequence that can be accommodated by the present invention.

Case 1 (see the first portion of FIG. 8): The stimulation pulse amplitude is just below or just above the heart's stimulation threshold. Accordingly, changes in the patient's physiological condition, the presence of myopotentials, electrical noise or the like may cause alternating capture and loss-of-capture events, i.e., a CBCBCB ... pattern, where C refers to capture associated with the primary pulse and B represents noncapture with delivery of a backup pulse. In the prior art, the pulse amplitude would not be increased since there are not two consecutive loss-of-capture events. However, in the present invention, an exemplary 2:3 criteria is satisfied after the fourth pulse of the sequence. Specifically, after 4 stimulation pulses, a pattern of CBCB has occurred which has 2 backup pulses (indicating a loss-of-capture) out of the last 3 pulses. Accordingly, the loss-of-capture recovery routine 142 will be executed. It is noteworthy that since only paced cycles are used in this determination, the presence of a PVC or even an intrinsic R-wave will not effect this determination. Accordingly, if a CBCIB sequence was presented (not shown), where "I" refers to a native or intrinsic complex which inhibits the pacemaker output, it would be processed as if a CBCB sequence occurred. Thus, this CBCIB pattern, treated as a CBCB pattern, would indicate a loss-of-capture since the intrinsic (I) cardiac cycle is not used in the loss-of-capture determination.

Figure 9:
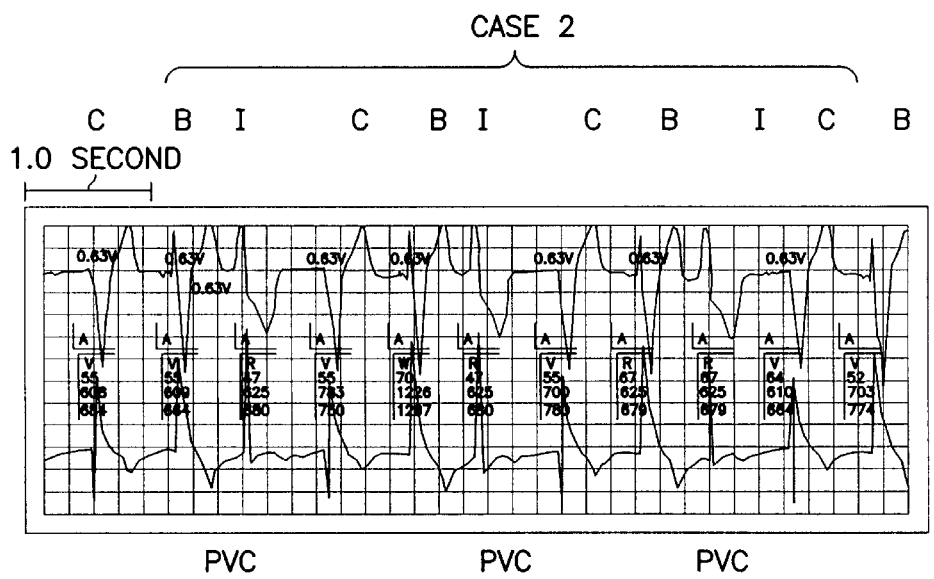
FIG. 9 is an exemplary intracardiac electrogram showing a trigeminy sequence of a loss-of-capture, a PVC, and a captured beat, a sequence that can be accommodated by the present invention.

Case 2 (see FIG. 9): The stimulation pulse is below threshold and the heart is experiencing PVCs from ectopic foci. As previously discussed, supernormal conduction may occur following each PVC due to an extended repolarization period or some other condition resulting in a transient decrease in the capture threshold. Accordingly, a below threshold stimulation pulse (i.e., a pulse that otherwise could not stimulate the heart) will now be able to stimulate the heart due to the PVC caused by an extension of the repolarization period or other reason. Accordingly, the below threshold stimulation pulse will now be able to generate an evoked response, i.e., the stimulation pulse will be captured. Following this captured pulse, the next below threshold pulse will again fail to capture and a backup pulse will be issued. Accordingly, a trigeminy pattern will occur as follows: BICBICBIC. Clearly, this sequence is contrary to the two consecutive loss-of-capture occurrence criteria of the prior art. However, since intrinsic events are not used in the determination made by embodiments of the present invention, this sequence is processed as the equivalent of a BCBCBC sequence. Using an exemplary 2:3 criteria, 2 out of the last 3 stimulation pulses will have not been captured with each being followed by the second backup pulse of this sequence. Accordingly, the loss-of-capture recovery routine 142 will be executed.

Figure 4:
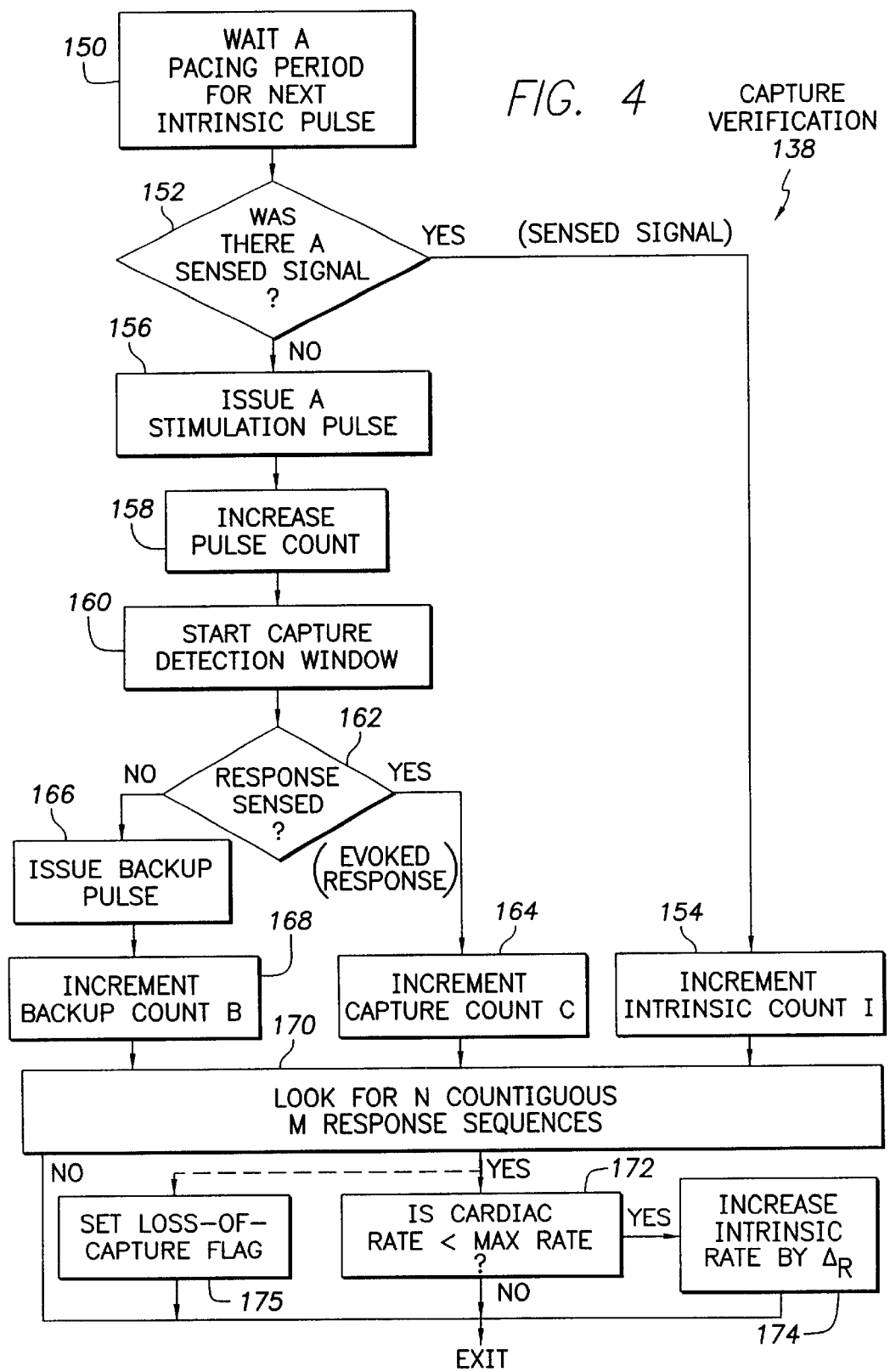
FIG. 4 is a flow chart of an exemplary capture verification routine as used in FIG. 3 for determining the loss-of-capture and capture criteria of the present invention.

FIG. 4 shows a more detailed explanation of an exemplary capture verification routine 138. A pacing rate is either determined by the intrinsic sinus rate of the atrium, indicated by P-waves, or by a rate determined by the pacemaker 70 and controlled by overdriving the intrinsic pacing rate of the atrium with atrial pulses from the atrial pulse generator 78. Overdriving the intrinsic pacing rate of the atrium can be useful, as discussed further below, to avoid PVCs from occurring during the autocapture/autothreshold routines. Initially, in block 150, the control/timing circuit 86 waits a period of time as determined by the current PV or AV (when the intrinsic rate has been increased) delays. In block 152, the control/timing circuit 86 notes if the ventricular channel sense amplifier 84 has sensed a signal. If a signal was sensed, an intrinsic event (I) is counted in block 154. If a signal was not sensed in block 152 by the end of the PV or AV delay, a ventricular stimulation pulse is issued in block 156 by the ventricular pulse generator 80 at the current stimulation amplitude. Optionally, in block 158 a stimulation pulse count can be incremented. However, since each stimulation pulse will either result in capture (C) or non-capture and a backup pulse (B), the number of stimulation pulses can be calculated as B+C. In block 160, a capture detection window starts. In an exemplary embodiment, the capture detection window is 60 ms which is comprised of a 14 ms absolute refractory period during which time the sense amplifier 84 is blanked from looking for evoked responses, followed by a 46 ms alert period during which the evoked responses are detectable. At the end of the capture detection window, it is determined in block 162 whether an evoked response was sensed by the ventricular channel sense amplifier 84. If there was an evoked response, a capture count (C) is incremented in block 164. Otherwise, if there was no evoked response, a high amplitude (e.g., 4.5 volt) backup pulse is issued in block 166 and a backup pulse (non-capture) count (B) is increased in block 168. (Blocks 170–174 refer to an alternative embodiment that includes special processing to avoid PVCs. This alternative embodiment will discussed later).

Figure 5:
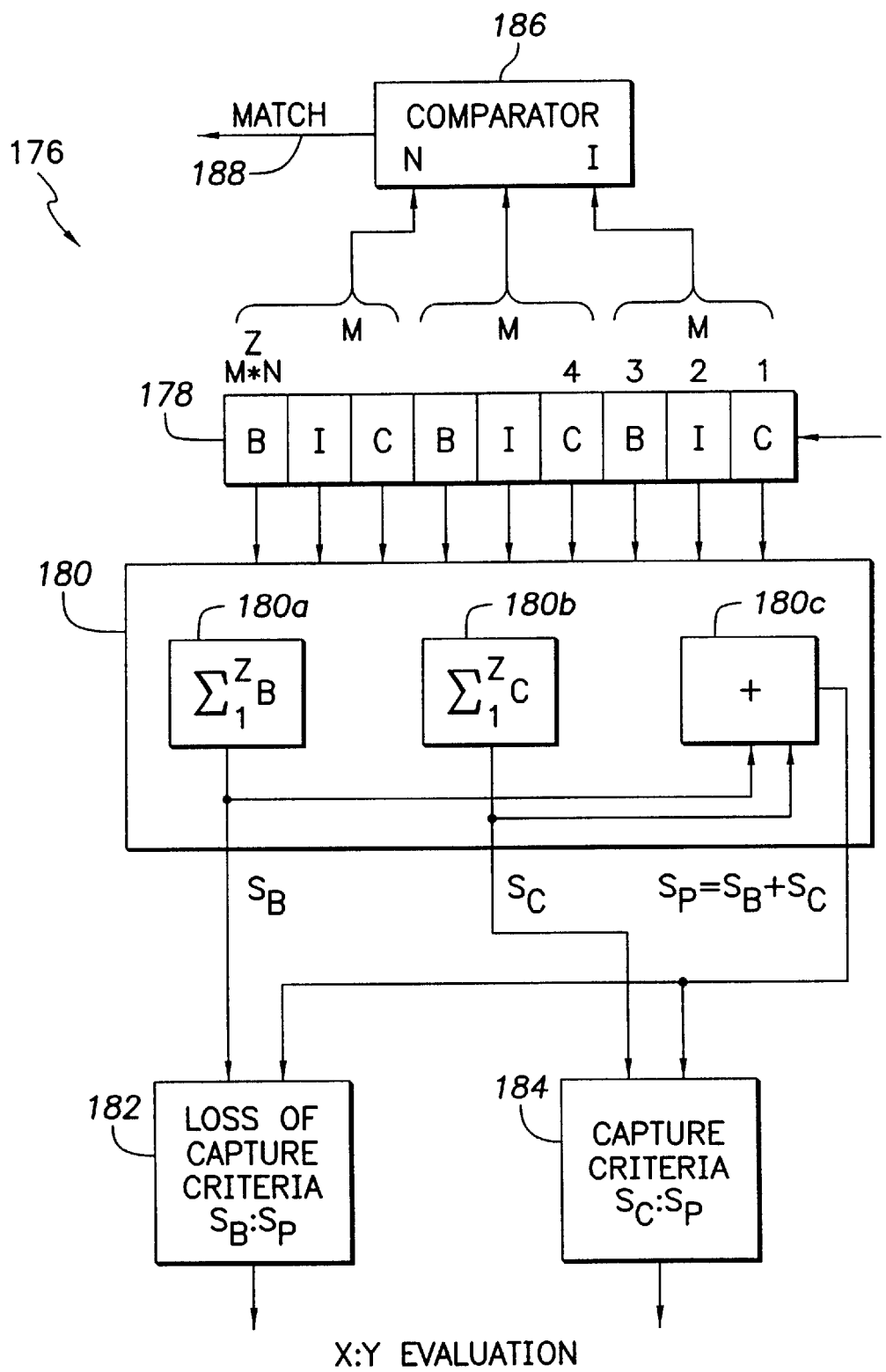
FIG. 5 is a block diagram of an exemplary structure for determining the loss-of-capture and capture criteria of the present invention as well as determining whether the cardiac pacing rate should be increased to break a repeating, e.g., trigeminy, pattern.

Block 140 (FIG. 3) may now evaluate the relationship of the most recent backup (B) and capture (C) counts to determine whether the loss-of-capture criteria has been met. FIG. 5 shows an exemplary method of making this determination with a status bit accumulator/evaluator 176. FIG. 5 can best be understood by considering it to represent a structure of hardware for processing status bits which represent what occurred during each cardiac cycle, i.e., whether an evoked response was detected (a capture beat (C)), an intrinsic beat (I) was detected, or a backup pulse (B) was generated when an evoked response was not detected. Such a hardware structure may be formed from a shift register for storing the status bits and adders and comparators or the like for evaluating the sums or sequences of status bits stored in the shift register. However, one of ordinary skill in the art will recognize that the best mode of implementing the status bit accumulator 176 would be as a software construct under the control of the control/timing circuit 86. In a software implementation, the status bits may be stored in a data portion of memory 100 under control of software instructions (in a control portion of the memory 100) executed by the control/timing circuit 86. The status bit accumulator 176 is primarily comprised of a Z-bit FIFO (First-In First-Out) buffer 178, a 3 stage summer 180 and decision blocks 182 and 184. The primary purpose of the status bit accumulator 176 is to determine if a prescribed loss-of-capture or capture criteria has been met. The criteria are designated herein as X:Y, i.e., whether X cardiac events out of the last Y cardiac events caused by stimulation pulses satisfied a loss-of-capture or capture criteria. Specifically, in making this determination, intrinsic cardiac events, e.g., R-waves or PVCs are not considered. The control/timing circuit 86 determines for each cardiac cycle whether a capture beat (C), backup pulse (B) or intrinsic beat (I) occurred. This status bit is sequentially stored into FIFO 178 so that a sample window of status bits for the last Z cardiac events (9 in the example shown in FIG. 5) are available for processing. Summers 180*a*–180*c* operate on the status bits stored in FIFO. 178 to determine three values. The first value $S_B$, generated by summer 180*a*, is the sum of all of the B bits in FIFO 178 and represents the number of backup pulses generated in the sample window. The second value $S_C$, generated by summer 180*b*, is the sum of all of the C bits in FIFO 178 and represents the number of captured pulse that were sensed in the sample window. The third value $S_P$, generated by summer 180*c*, is the sum of the values $S_B$. and $S_C$ and represents the number of paced cardiac cycles. Significantly, $S_P$ does not include intrinsic (I) responses which could represent PVCs or other non-paced cardiac events. Decision blocks 182 and 184 evaluate the X:Y criteria based upon the $S_B$, $S_C$ and $S_P$ values. For example, decision block 182 determines $S_B$:$S_P$, the number of backup, i.e., non-captured, pulses which occurred in the last $S_P$ paced cardiac cycles and decision block 184 determines $S_C$:$S_P$, the number of captured pulses which occurred in the last $S_P$ paced cardiac cycles. In FIG. 5, status bits from the aforementioned trigeminy pattern are shown entering into the right side of FIFO 178 and moving from the right to the left of FIFO 178. Therefore, at the current cycle of the 9 cycle sample window shown, there are 3 backup pulses (B), 3 intrinsic pulses (I), and 3 captured pulses (C). Accordingly, after ignoring the cardiac cycles with intrinsic (I) beats, 3 out of the last 6 pulsed cycles were captured (3:6) and 3 out of the last 6 pulsed cycles were not captured (3:6). If, for example, 3:6 was an acceptable criteria for recognizing a loss-of-capture, 4:6, 5:6 and 6:6 which represent a higher loss-of-capture rate would also satisfy a 3:6 criteria. Accordingly, a loss-of-capture (or capture) criteria may also be represented by a percentage threshold which would satisfy the criteria if it was met or exceeded. The use of such an approach, is additionally apparent when it is considered that some cycle sequences could include a smaller or larger amount of intrinsic (I) cycles. For example, if the most recent intrinsic cycle was instead a non capture cycle, the observed X:Y value would have been 4:7 which would represent a higher loss-of-capture percentage. Alternatively, a table 101 could be generated and stored in memory 100 which would correspond to values that exceeded a criteria for a given sample window size. For example, if 3:6 satisfies the criteria on a 9 cycle sample window, the criteria would be greater than or equal to 50% or the following X:Y values:

| | | | |
|---|---|---|---|
| 3:6 | | | |
| 4:6 | 4:7 | 4:8 | |
| 5:6 | 5:7 | 5:8 | 5:9 |
| 6:6 | 6:7 | 6:8 | 6:9 |
| | | 7:8 | 7:9 |
| | | | 8:9 |
| | | | 9:9 |

Either a table look up or percentage value comparison are considered to be equivalent methods of evaluating whether the criteria have been met.

Operating on a smaller sample window will generally allow the criteria to met in fewer cardiac cycles and thus limit the number of required backup pulses generated while the pulse amplitude threshold is being determined. For example, as previously described, a 2:3 decision with a 4 cycle sample window would have been able to respond within 4 cardiac cycles to the trigeminy pattern. Additionally, the percentage criteria would now be 66.67%, a more definitive criteria than 50%. Accordingly, a preferred criteria for responding to the afore-described patterns is a 2:3 criteria and a 4 sample window.

However, such a criteria may be too responsive in the presence of electrical noise, myopotentials or the like. Therefore, an alternative embodiment includes the capability of recognizing a trigeminy pattern or the like and taking action to break the pattern before making a capture/loss-of-capture (LOC) determination. In this alternative mode, shown in blocks 170–174 of FIG. 4, the apparatus looks for a repeating, e.g., a trigeminy, pattern and if it is detected, increases the cardiac rate (by atrial pacing with the atrial pulse generator 78) to attempt to break the pattern. Generally, by increasing the cardiac rate by overdriving the intrinsic rate, PVCs can be suppressed. Once the PVCs are suppressed, supernormal conduction will no longer occur and loss-of-capture/capture decisions will correspond to the actual threshold of the cardiac tissue. Preferably, the cardiac rate will not be allowed to exceed a predetermined maximum rate, e.g., 100 beats per minute (bpm), in this mode. Preferably, this rate will be a programmable parameter selectable by the clinician.

For example, block 170 determines if a sequence of N contiguous predefined sequences of M status responses have been determined. For the example of FIG. 5, this would be 3 contiguous predefined 3 cycle (BIC) sequences. A comparator 186 (FIG. 6) could be used to compare the patterns generated in N contiguous sequences to each other and the predefined, e.g., BIC, pattern or other pattern that preferably included at least one intrinsic (I) wave. If found, a match signal 188 would be generated to show that the criteria of block 170 was satisfied. In block 172, it is determined whether the cardiac rate exceeded a maximum rate, e.g., 100 bpm. If the maximum rate was not exceeded, then the cardiac rate would be increased by a value $\Delta_R$, e.g., 10 bpm, in block 174 by atrial pacing (as long as that increase would not cause a cardiac rate above the maximum allowed rate for testing purposes). If the trigeminy pattern is successfully broken, PVCs and the associated supernormal conduction will stop occurring. Accordingly, the pattern would switch to a BBB pattern from the BIC pattern since the intrinsic, i.e., PVC, waves would stop and the following cardiac cycles would revert to showing the actual below threshold condition of the stimulation pulses. In this alternative embodiment, a larger, e.g., 9 cycle, sample window, would preferably be used as well as a more restrictive, e.g., 4:6, loss-of-capture criteria. In this example, a BIC pattern would not satisfy the 4:6 loss-of-capture criteria. However, once the BIC pattern has repeated N, i.e., 3, times, the cardiac pacing rate would increase and break the trigeminy pattern. Once the pattern is broken, the loss-of-capture value would exceed the 3:6 criteria and the loss-of-capture recovery routine 140 would then be invoked.

In a next alternative implementation, detection of a trigeminy pattern or the like as described in reference to block 170 can be used to identify a loss-of-capture. Accordingly, when the criteria of block 170 have been satisfied, a loss-of-capture status flag can be set in block 175. Subsequently, this status flag can be used to identify a loss-of-capture in loss-of-capture criteria blocks, e.g., 140.

Figure 6:
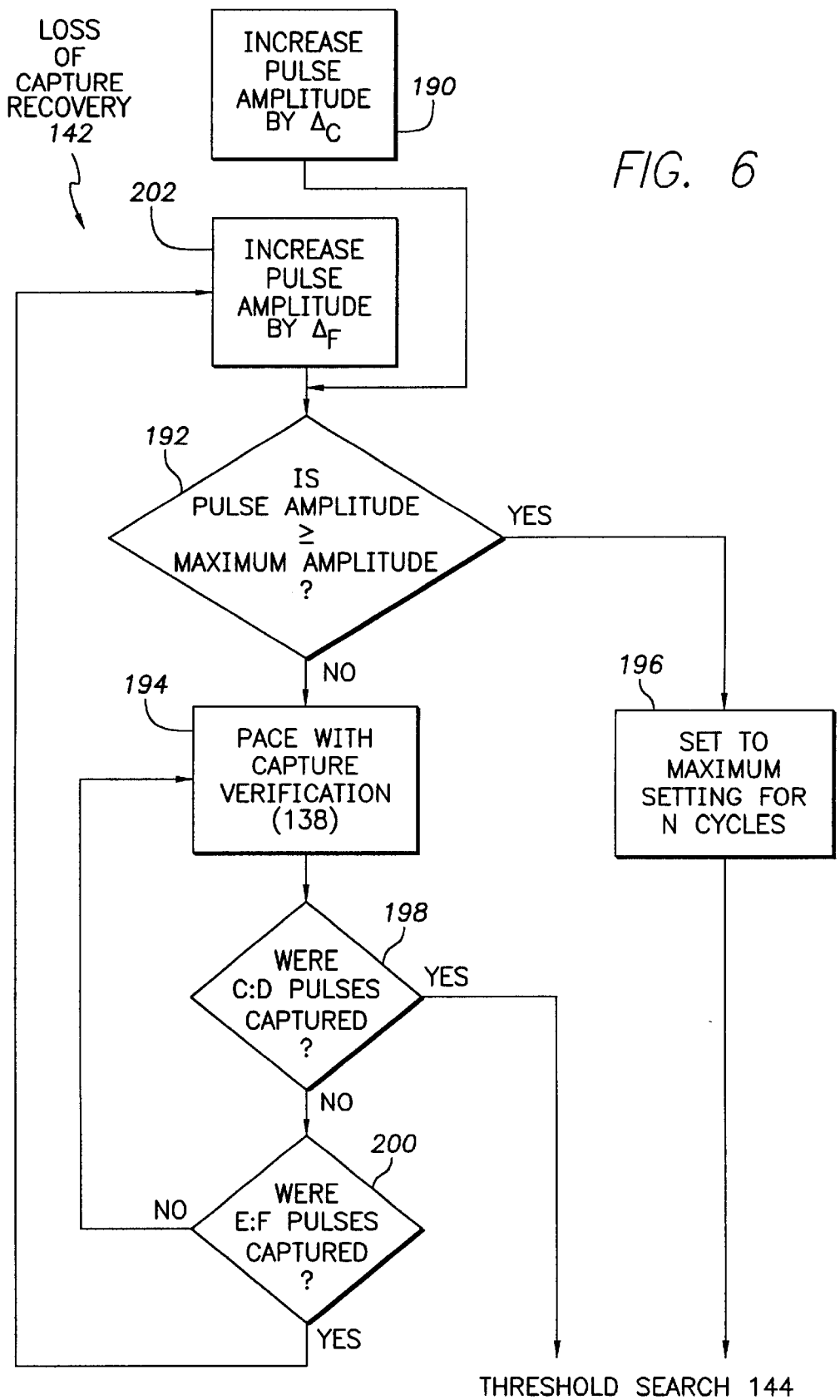
FIG. 6 is an exemplary loss-of-capture recovery routine that incorporates the advanced loss-of-capture and capture criteria of the present invention.

FIGS. 6 and 7 respectively show an exemplary loss-of-capture recovery routine 142 and a threshold search routine 144 which include the advanced loss-of-capture and capture criteria of the present invention. The loss-of-capture recovery routine 142 begins once the loss-of capture criteria of block 140 has been satisfied. In block 190, the stimulation pulse amplitude is first increased by a coarse value $\Delta_C$, e.g., 0.250 volts. Providing that the pulse amplitude does not exceed a maximum value ramp up value, e.g., 3.875 volts although this value may be higher, in block 192, a stimulation pulse is delivered at block 194 during the next cardiac cycle according to the preset AV or PV delay. If the maximum pulse amplitude value has been reached or exceeded, the stimulation pulse is set to a maximum value in block 196 and the threshold search routine 144 is invoked. Otherwise, in blocks 198 and 200, it is respectively determined if C:D pulses were captured and E:F pulses were not captured. If the capture criteria of block 198 is satisfied, signifying that capture has been regained, the threshold search routine 144 is invoked. Otherwise, if loss-of-capture still exists according to the criteria of block 200, the pulse amplitude is increased by a fine value $\Delta_F$, e.g., 0.125 volts, in block 202 and the process continues. Preferably, these criteria are evaluated as previously discussed with 2:3 being a preferred value for the E:F criteria and 2:2 for the C:D criteria. Accordingly, the loss-of-capture recovery routine will be more responsive than the prior art in causing the stimulation amplitude to ramp up to a value above the stimulation threshold. For example, while a prior art device would not increase the stimulation pulse amplitude (see the first portion of FIG. 8) if the pulse amplitude was marginally below threshold such that a BCBC sequence was sensed, the present invention will recognize such a sequence as satisfying the criteria (e.g., 2:3) for increasing the pulse amplitude. Accordingly, the ramp up criteria has been biased upwards.

Figure 7A:
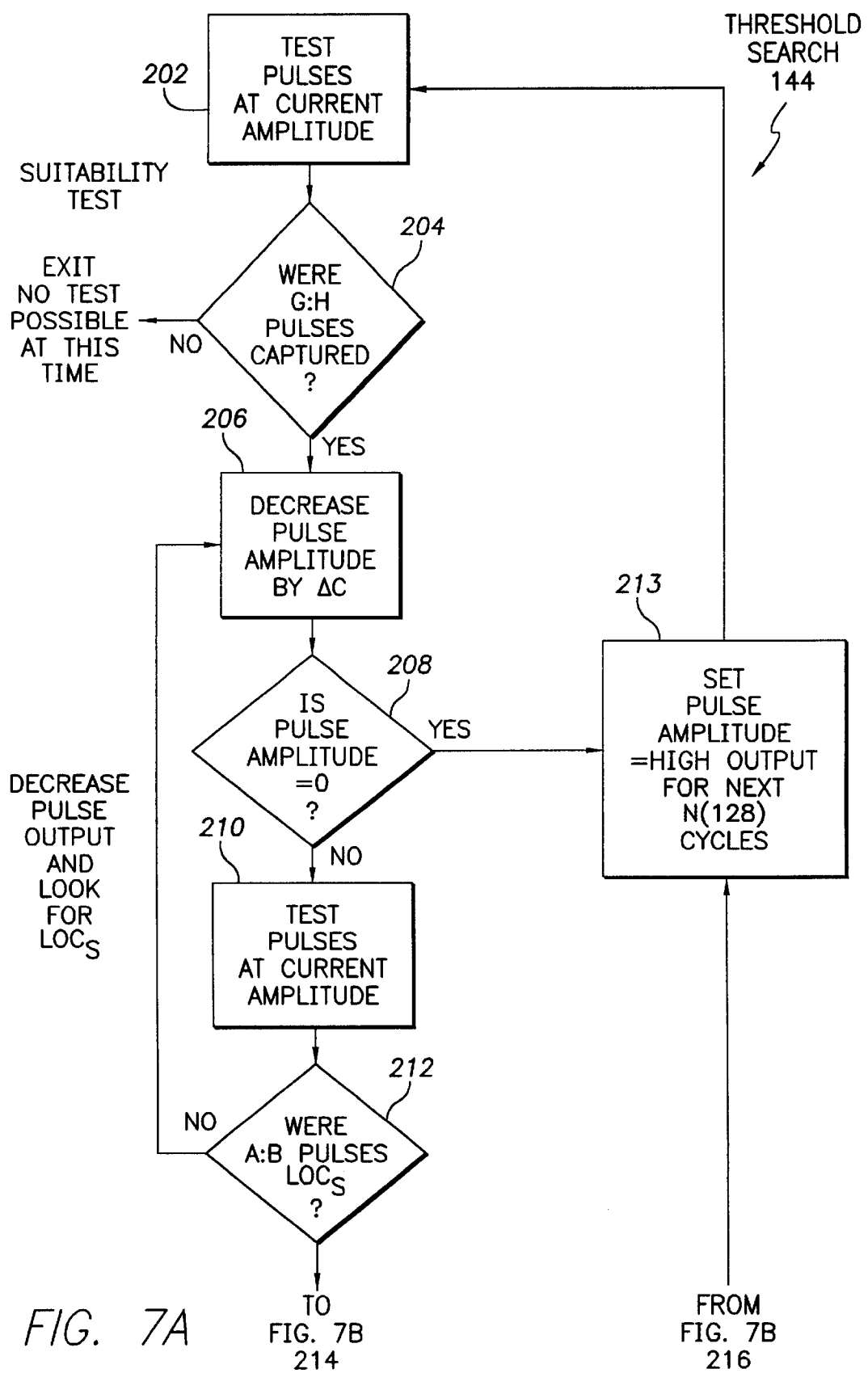
FIGS. 7A and 7B comprise an exemplary threshold search routine that incorporates the advanced loss-of-capture and capture criteria of the present invention.
Figure 7B:
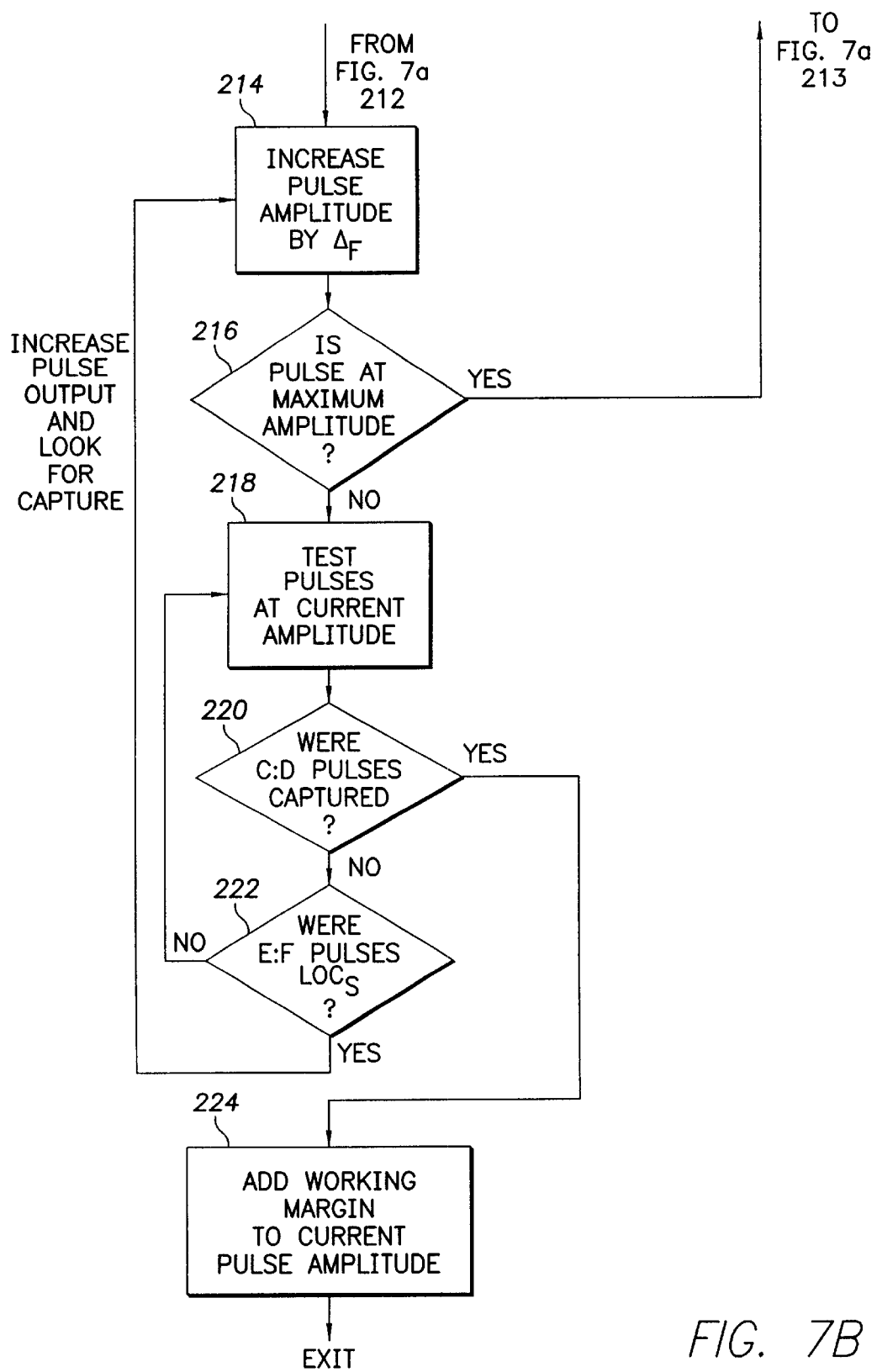

FIGS. 7A and 7B show an exemplary threshold search routine 144 that incorporates the loss-of-capture, capture criteria of the present invention. As previously discussed, the threshold search routine 144 is either periodically invoked, e.g., once a day, or invoked following each invocation of the loss-of-capture recovery routine 142. Initially, a suitability test occurs in block 202 and 204 which determines if a capture criteria is satisfied. This capture criteria is evaluated in a similar manner to the previously described (X:Y)

loss-of-capture criteria. In block 204, the criteria (G:H) is whether G out of the last H pulses were captured. If the criteria is not satisfied after a specified number of pulses, the test is deferred until a later time. In a preferred embodiment, this criteria is set to a 2:3 value which biases the test to occur when possible.

In a next portion (blocks 206–212) of the threshold search routine 144, the pulse amplitude is periodically decreased by a coarse value, $\Delta_C$, e.g., 0.250 volts, until an A:B, e.g., a 2:3, loss-of-capture criteria is satisfied which identifies a non-capture level. If the pulse amplitude is decreased to zero, the routine branches to block 213 where the pulse amplitude is reset to a high output (e.g., 4.5 volts) for the next N (e.g., 128) cycles before restarting the routine. Finally, in blocks 214–222 the pulse amplitude is increased by a fine value $\Delta_F$, e.g., 0.125 volts, to identify a capture level in a similar manner to that described in reference to the loss-of-capture recovery routine 142. As previously discussed, the C:D capture and E:F loss-of-capture criteria, preferably 2:2 and 2:3 respectively, can be set to provide an improved autocapture/autothreshold capability and specifically to enable the systems of the present invention to respond to the circumstances presented in reference to FIGS. 8 and 9. As a final step of the threshold search routine 144, a working margin, e.g., 0.250 volts, is added in block 224 to the capture level. This value is then used for stimulation pulses until either the threshold search routine 144 is activated, e.g., according to predetermined schedule, or a loss-of-capture occurs which activates the loss-of-capture recovery routine 142.

Accordingly, what has been shown is an improved criteria for performing an autocapture/autothreshold procedure in an implantable cardiac stimulation device. While the invention has been described by means of specific embodiments and applications thereof, it is understood that numerous modifications and variations could be made thereto by those skilled in the art without departing from the spirit and scope of the invention. Alternative X:Y loss of capture criteria are also considered to be within the scope of the present invention. For example, to avoid fusion beats it may be desirable to have X=Y with X and Y greater than 2 such that a loss of capture for 3 or more consecutive beats would be required before increasing the stimulation pulse amplitude. It is therefore to be understood that within the scope of the claims, the invention may be practiced otherwise than as specifically described herein.

What is claimed is:

1. An implantable cardiac stimulation device for stimulating a patient's heart during a cardiac cycle through at least one electrode adapted for electrical contact with selected cardiac tissue, the stimulation device comprising:
   a pulse generator electrically coupled to the electrode and configured to generate stimulation pulses at a controlled amplitude and rate to thereby stimulate the patient's heart;
   a detection circuit electrically coupled to the electrode and configured to receive cardiac signals for determining the presence or absence of an evoked response to each of the stimulation pulses, wherein the detection circuit is further configured to determine the status, for each cardiac cycle, of the presence of an evoked response to each stimulation pulse, the absence of an evoked response to each stimulation pulse, or the presence of an intrinsic cardiac signal without a stimulation pulse; and
   a controller coupled to the pulse generator for increasing the stimulation pulse amplitude when a first specified criteria has been met, wherein the first specified criteria is the absence of evoked responses from X out of the last Y stimulation pulses where Y is a value greater than 2 and X is a value less than Y, wherein the controller determines the presence of a predetermined sequence of status determinations from M consecutive cardiac cycles, and further determines the presence of N contiguous occurrences of the specified sequence of M status determinations, wherein the controller is configured to increase the controlled rate in response thereto.

2. The cardiac stimulation device of claim 1 wherein:
   the detection circuit detects the presence of an evoked response during a detection time period following each stimulation pulse; and wherein
   the controller causes the pulse generator to generate a backup pulse at the end of each detection time period when an evoked response is not detected.

3. The cardiac stimulation device of claim 2 wherein the backup pulse is set to a predetermined maximum amplitude.

4. An implantable cardiac stimulation device for stimulating a patient's heart during a cardiac cycle through at least one electrode adapted for electrical contact with selected cardiac tissue, the stimulation device comprising:
   a pulse generator electrically coupled to the electrode and configured to generate stimulation pulses at a controlled amplitude and rate to thereby stimulate the patient's heart;
   a detection circuit electrically coupled to the electrode and configured to receive cardiac signals for determining the presence or absence of an evoked response to each of the stimulation pulses;
   a controller coupled to the pulse generator for increasing the stimulation pulse amplitude when a first specified criteria has been met, wherein the first specified criteria is the absence of evoked responses from X out of the last Y stimulation pulses where Y is a value greater than 2 and X is a value less than Y; and
   wherein the controller is configured to periodically adjust the stimulation pulse amplitude by performing a threshold search to determine a stimulation pulse amplitude capable of causing an evoked response, the threshold search including detecting a non-capture pulse amplitude level according to a second specified criteria and a capture pulse amplitude level according to a third specified criteria.

5. The cardiac stimulation device of claim 4 wherein the second specified criteria is A out of the last B stimulation pulses not generating evoked responses, wherein B is greater than 2 and A is less than B.

6. The cardiac stimulation device of claim 4 wherein the third specified criteria is C out of the last D stimulation pulses generating evoked responses, wherein D is greater than 2 and C is less than D.

7. The cardiac stimulation device of claim 4 wherein the stimulation pulse amplitude is set following the threshold search to a predetermined value above the capture pulse amplitude level.

8. The cardiac stimulation device of claim 4 wherein the controller causes the threshold search to be performed following the increase of the stimulation pulse amplitude performed in response to the absence of evoked responses to X out of the last Y stimulation pulses.

9. A method for determining the threshold value for a stimulation pulse for stimulating a patient's heart during a cardiac cycle through at least one electrode adapted for electrical contact with selected cardiac tissue, the method comprising:

periodically stimulating the patient's heart with a stimulation pulse, the stimulation pulse having a controlled amplitude and rate;

detecting the presence or absence of an evoked response generated by the patient's heart in response to the stimulation pulse during a detection window;

increasing the amplitude of the stimulation pulse in response to a first specified evoked response criteria, wherein the first specified criteria is the absence of evoked responses from X out of the last Y stimulation pulses where Y is a value greater than 2 and X is a value less than Y; and determining for a sequence of cardiac cycles, status responses indicating: C, the number of pulses having evoked responses, I, the number of detected intrinsic signals that were not in response to a stimulation pulse, B, the number of cardiac cycles that included backup pulses, and Y, the number of cardiac cycles having stimulation pulses, wherein Y equals B+C.

10. A method for determining the threshold value for a stimulation pulse for stimulating a patient's heart during a cardiac cycle through at least one electrode adapted for electrical contact with selected cardiac tissue, the method comprising:

periodically stimulating the patient's heart with a stimulation pulse, the stimulation pulse having a controlled amplitude and rate;

detecting the presence or absence of an evoked response generated by the patient's heart in response to the stimulation pulse during a detection window;

increasing the amplitude of the stimulation pulse in response to a first specified evoked response criteria, wherein the first specified criteria is the absence of evoked responses from X out of the last Y stimulation pulses where Y is a value greater than 2 and X is a value less than Y;

detecting a status response for each cardiac cycle, wherein the status response indicates whether the stimulation pulse had an evoked response, the stimulation pulse did not have an evoked response, or an intrinsic signal was detected without a stimulation pulse;

determining the presence of a predetermined sequence of status responses from M consecutive cardiac cycles;

determining the presence of N contiguous occurrences of the specified sequence of M status responses; and increasing the controlled stimulation rate in response to the presence of the N contiguous occurrences of the predetermined sequence of M status responses.

11. The method of claim 10 additionally comprising the step of generating a backup pulse following the detection window if no evoked response is detected.

12. The method of claim 11 wherein the backup pulse is set to a predetermined maximum amplitude.

13. The method of claim 10 further comprising the step of periodically adjusting the stimulation pulse amplitude by performing a threshold search to determine a stimulation pulse amplitude capable of causing an evoked response, the threshold search including detecting a non-capture pulse amplitude level according to a second specified criteria and a capture pulse amplitude level according to a third specified criteria.

14. The method of claim 13 wherein the second specified criteria is A out of the last B stimulation pulses not generating evoked responses, wherein B is greater than 2 and A is less than B.

15. The method of claim 13 wherein the third specified criteria is C out of the last D stimulation pulses generating evoked responses, wherein D is greater than 2 and C is less than D.

16. The method of claim 13 wherein the step of periodically performing a threshold search occurs is performed following the step of increasing the amplitude of the stimulation pulse in response to the first specified criteria.

17. An implantable cardiac stimulation device for stimulating a patient's heart during a cardiac cycle through at least one electrode implanted in electrical contact with selected cardiac tissue, the stimulation device comprising:

a pulse generator electrically coupled to the electrode and configured to generate stimulation pulses at a controlled amplitude and rate to thereby stimulate the patient's heart;

a detection circuit electrically coupled to the electrode and configured to receive cardiac signals for determining the presence or absence of an evoked response in response to each of the stimulation pulses;

storing means for storing a status response for a sequence of cardiac cycles, the status response comprising whether an evoked response (C) was detected, whether a backup pulse (B) was generated, or whether an intrinsic signal (I) was detected without a stimulation pulse;

evaluation means for determining whether a criteria is satisfied based upon the stored status responses;

a controller for causing the pulse generator to increase the amplitude of the stimulation pulses in response to a first specified criteria, wherein the first specified criteria is the absence of evoked responses from X out of the last Y stimulation pulses where Y is a value greater than 2 and X is a value less than Y.

18. The cardiac stimulation device of claim 17 wherein the storing means is a First-In First-Out (FIFO) buffer formed from a shift register.

19. The cardiac stimulation device of claim 17 wherein the storing means is a First-In First-Out (FIFO) buffer formed from a sequence of software instructions executed by the controller.

20. The cardiac stimulation device of claim 17 wherein:

the detection circuit detects the presence of evoked responses during a detection window following each stimulation pulse; and wherein the controller causes the pulse generator to generate a backup pulse at the end of each detection window when an evoked response is not detected.

21. The cardiac stimulation device of claim 20 wherein the backup pulse is set to a predetermined maximum amplitude.

22. The cardiac stimulation device of claim 17 wherein the storing means further comprises means to detect a predetermined sequence of status responses from M consecutive cardiac cycles and means for determining the presence of N contiguous occurrences of the predetermined sequence of M status responses, wherein the controller is configured to increase the controlled stimulation rate in response thereto.

23. The cardiac stimulation device of claim 17 wherein the controller is configured to periodically adjust the stimulation pulse amplitude by performing a threshold search to determine a stimulation pulse amplitude capable of causing an evoked response, the threshold search including detecting a non-capture pulse amplitude level according to a second specified criteria and a capture pulse amplitude level according to a third specified criteria.

24. The cardiac stimulation device of claim 23 wherein the second specified criteria is A out of the last B stimulation pulses not generating evoked responses, wherein B is greater than 2 and A is less than B.

25. The cardiac stimulation device of claim 23 wherein the third specified criteria is C out of the last D stimulation pulses generating evoked responses, wherein D is greater than 2 and C is less than D.

26. The cardiac stimulation device of claim 23 wherein the controlled amplitude is set following the threshold search to a predetermined value above the capture pulse amplitude level.

27. The cardiac stimulation device of claim 23 wherein the controller causes the threshold search to be performed following the increase of the stimulation pulse amplitude performed in response to the absence of evoked responses to X out of the last Y stimulation pulses.

28. An implantable cardiac stimulation device for stimulating a patient's heart during a cardiac cycle through at least one electrode implanted in electrical contact with selected cardiac tissue, the stimulation device comprising:
 a pulse generator electrically coupled to the electrode and configured to generate stimulation pulses at a controlled amplitude and rate to thereby stimulate the patient's heart;
 a detection circuit electrically coupled to the electrode and configured to receive cardiac signals for determining the presence or absence of an evoked response in response to each of the stimulation pulses;
 storing means for storing a status response for a sequence of cardiac cycles, the status response comprising whether an evoked response (C) was detected, whether a backup pulse (B) was generated, or whether an intrinsic signal (I) was detected without a stimulation pulse;
 evaluation means for determining whether a predetermined criteria is satisfied based upon the stored status responses, wherein the criteria is the detection of a predetermined sequence of status responses from M consecutive cardiac cycles and the detection of N contiguous occurrences of the predetermined sequence of M status responses; and
 a controller for causing the pulse generator to increase the amplitude of the stimulation pulses in response to the predetermined criteria.

29. An implantable cardiac stimulation device for stimulating a patient's heart during a cardiac cycle through at least one electrode implanted in electrical contact with selected cardiac tissue, the stimulation device comprising:
 a pulse generator electrically coupled to the electrode and configured to generate stimulation pulses at a controlled amplitude and rate to thereby stimulate the patient's heart;
 a detection circuit electrically coupled to the electrode and configured to receive cardiac signals for determining the presence or absence of an evoked response to each of the stimulation pulses; and
 a controller coupled to the pulse generator for increasing the stimulation pulse amplitude when a first specified criteria has been met, wherein the first specified criteria is the absence of evoked responses from X out of the last Y stimulation pulses where Y is a value greater than 2 and X is a value equal to Y.

30. An implantable stimulation device for stimulating a patient's body tissue through at least one electrode implanted in electrical contact with selected body tissue, the stimulation device comprising:
 a pulse generator electrically coupled to the electrode and configured to generate stimulation pulses at a controlled amplitude and rate to thereby stimulate the patient's body tissue;
 a detection circuit electrically coupled to the electrode and configured to receive signals for determining the presence or absence of an evoked response to each of the stimulation pulses, wherein the detection circuit is further configured to determine the status, for each cardiac cycle, of the presence of an evoked response to each stimulation pulse, the absence of an evoked response to each stimulation pulse, or the presence of an intrinsic cardiac signal without a stimulation pulse; and
 a controller coupled to the pulse generator for increasing the stimulation pulse amplitude when a first specified criteria has been met, wherein the first specified criteria is a repetitive pattern of the absence of evoked responses from X out of the last Y stimulation pulses where Y is a value greater than 2 and X is a value less than Y, wherein the controller determines the presence of a predetermined sequence of status determinations from M consecutive cardiac cycles, and further determines the presence of N contiguous occurrences of the specified sequence of M status determinations, wherein the controller is configured to increase the controlled rate in response thereto.

31. A method for determining the threshold value for a stimulation pulse for stimulating a patient's body tissue through at least one electrode implanted in electrical contact with selected body tissue, the method comprising the steps of:
 periodically stimulating the patient's body tissue with a stimulation pulse, the stimulation pulse having a controlled amplitude and rate;
 detecting the presence or absence of an evoked response generated by the patient's body tissue in response to the stimulation pulse during a detection window;
 increasing the amplitude of the stimulation pulse in response to a first specified evoked response criteria, wherein the first specified criteria is the absence of evoked responses from X out of the last Y stimulation pulses where Y is a value greater than 2 and X is a value less than Y;
 detecting a status response for each cardiac cycle, wherein the status response indicates whether the stimulation pulse had an evoked response, the stimulation pulse did not have an invoked response, or an intrinsic signal was detected without a stimulation pulse;
 determining the presence of a predetermined sequence of status responses from M consecutive cardiac cycles;
 determining the presence of N contiguous occurrences of the specified sequence of M status responses; and
 increasing the controlled stimulation rate in response to the presence of the N contiguous occurrences of the predetermined sequence of M status responses.

32. An implantable stimulation device for stimulating a patient's body tissue through at least one electrode implanted in electrical contact with selected body tissue, the stimulation device comprising:
 a pulse generator electrically coupled to the electrode and configured to generate stimulation pulses at a controlled amplitude and rate to thereby stimulate the patient's body tissue;
 a detection circuit electrically coupled to the electrode and configured to receive signals for determining the presence or absence of an evoked response in response to each of the stimulation pulses;

storing means for storing a status response for a sequence of stimulation cycles, the status response comprising whether an evoked response (C) was detected, whether a backup pulse (B) was generated, or whether an intrinsic signal (I) was detected without a stimulation pulse;

evaluation means for determining whether a criteria is satisfied based upon the stored status responses;

a controller for causing the pulse generator to increase the amplitude of the stimulation pulses in response to a first specified criteria, wherein the first specified criteria is the absence of evoked responses from X out of the last Y stimulation pulses where Y is a value greater than 2 and X is a value less than Y.

33. An implantable stimulation device for stimulating a patient's body tissue through at least one electrode implanted in electrical contact with selected body tissue, the stimulation device comprising:

a pulse generator electrically coupled to the electrode and configured to generate stimulation pulses at a controlled amplitude and rate to thereby stimulate the patient's body tissue;

a detection circuit electrically coupled to the electrode and configured to receive signals for determining the presence or absence of an evoked response in response to each of the stimulation pulses;

storing means for storing a status response for a sequence of stimulation cycles, the status response comprising whether an evoked response (C) was detected, whether a backup pulse (B) was generated, or whether an intrinsic signal (I) was detected without a stimulation pulse;

evaluation means for determining whether a predetermined criteria is satisfied based upon the stored status responses, wherein the criteria is the detection of a predetermined sequence of status responses from M consecutive stimulation cycles and the detection of N contiguous occurrences of the predetermined sequence of M status responses; and a controller for causing the pulse generator to increase the amplitude of the stimulation pulses in response to the predetermined criteria.

34. An implantable cardiac stimulation device for stimulating a patient's heart during a cardiac cycle through at least one electrode adapted for electrical contact with selected cardiac tissue, the stimulation device comprising:

a pulse generator, electrically coupled to the electrode, configured to generate stimulation pulses at a controlled amplitude and rate to thereby stimulate the patient's heart;

a detection circuit, electrically coupled to the electrode and configured to receive cardiac signals, that detects capture events or loss-of-capture events in response to each'of the stimulation pulses; and a controller, coupled to the pulse generator, for adjusting one of the stimulation pulse amplitude or the rate when a first specified criteria has been met, the first specified criteria being a repetitive pattern of "X" captured events followed by "Y" loss-of-capture events.

35. The implantable cardiac stimulation of claim 34, wherein:

the repetitive pattern is a bigeminy-type repetitive pattern having one captured event followed by one loss-of-capture event out of two consecutive cardiac cycles.

36. The implantable cardiac stimulation of claim 34, wherein:

the repetitive pattern is a trigeminy-type repetitive pattern having at least one captured event followed by at least one loss-of-capture event out of three consecutive cardiac cycles.

37. The implantable cardiac stimulation of claim 34, wherein:

the repetitive pattern is a pattern having "N" contiguous occurrences of at least one captured event followed by at least one loss-of-capture event out of each "M" consecutive cardiac cycles.

38. The implantable cardiac stimulation of claim 34, wherein:

the controller selectively ignores intrinsic events as part of the repetitive pattern.

39. The implantable cardiac stimulation of claim 34, wherein:

the controller selectively ignores premature ectopic events as part of the repetitive pattern.

40. A method for determining the threshold value for a stimulation pulse for stimulating a patient's body tissue through at least one electrode implanted in electrical contact with selected body tissue, the method comprising the steps of:

periodically stimulating the patient's body tissue with a stimulation pulse, the stimulation pulse having a controlled amplitude and rate;

detecting captured events and loss-of-capture events in response to the stimulation pulse during a detection window;

increasing the amplitude of the stimulation pulses when a repetitive pattern of "X" captured events followed by "Y" loss-of-capture events occurs.

41. A method for determining the threshold value for a stimulation pulse for stimulating a patient's body tissue through at least one electrode implanted in electrical contact with selected body tissue, the method comprising the steps of:

periodically stimulating the patient's body tissue with a stimulation pulse, the stimulation pulse having a controlled amplitude and rate;

detecting captured events and loss-of-capture events in response to the stimulation pulse during a detection window;

increasing the rate of the stimulation pulses when a repetitive pattern of "X" captured events followed by "Y" loss-of-capture events occurs.

* * * * *